United States Patent [19]

Sternbach et al.

[11] 3,954,728

[45] May 4, 1976

[54] PREPARATION OF TRIAZOLO BENZODIAZEPINES AND NOVEL COMPOUNDS

[75] Inventors: Leo Henryk Sternbach, Upper Montclair; Armin Walser, West Caldwell, both of N.J.

[73] Assignee: Hoffman-La Roche Inc., Nutley, N.J.

[22] Filed: Jan. 13, 1975

[21] Appl. No.: 540,756

Related U.S. Application Data

[62] Division of Ser. No. 271,434, July 13, 1972, Pat. No. 3,879,406.

[52] U.S. Cl. .................. 260/239 BD; 260/296 B
[51] Int. Cl.² ............... C07D 213/00; C07D 243/20
[58] Field of Search ...... 260/296 T, 239 BD, 296 B, 260/308 R

[56] References Cited

UNITED STATES PATENTS

| 3,701,782 | 10/1972 | Hester | 260/308 R |
| 3,879,406 | 4/1975 | Sternbach et al. | 260/296 T |

FOREIGN PATENTS OR APPLICATIONS

| 2,335,281 | 1/1974 | Germany | 260/296 T |

*Primary Examiner*—John D. Randolph
*Attorney, Agent, or Firm*—Samuel L. Welt; Bernard S. Leon

[57] ABSTRACT

Novel preparations of triazolobenzodiazepines are disclosed. Novel 6-pyridyl-4H-triazolo[4,3-a]-1,4-benzodiazepines and novel intermediates are also disclosed which are useful as anti-convulsants, muscle relaxants and sedative agents.

6 Claims, No Drawings

PREPARATION OF TRIAZOLO BENZODIAZEPINES AND NOVEL COMPOUNDS

This is a division of application Ser. No. 271,434 filed July 13, 1972, now U.S. Pat. 3,879,406 granted Apr. 22, 1975.

DETAILED DESCRIPTION OF THE INVENTION

This invention relates to novel 6-pyridyl-triazolobenzodiazepines and to novel processes for making the foregoing, which processes are additionally useful in the preparation of other 6-aryl-triazolobenzodiazepines. Also included within the purview of the present invention are novel intermediates useful in the preparation of such triazolobenzodiazepines.

More particularly, the present invention relates to a process for preparing a 6-aryl-triazolobenzodiazepine including novel 6-pyridyl compounds selected from the group consisting of compounds of the formulae

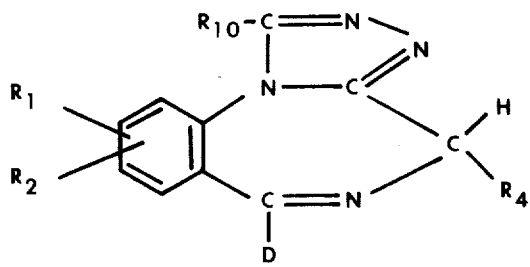

I and

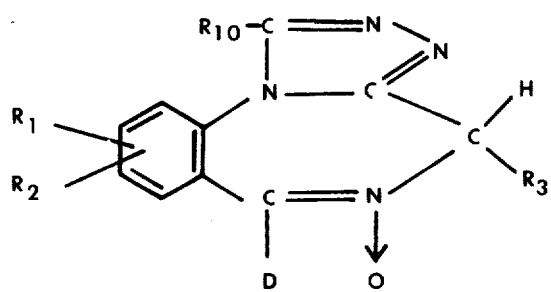

Ia and pharmaceutically acceptable acid addition salts thereof
wherein D is selected from the group consisting of

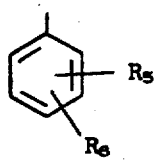 and 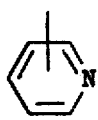

$R_1$ and $R_2$ are each selected from the group consisting of hydrogen, halogen, nitro and trifluoromethyl; $R_3$ is selected from the group consisting of hydrogen and lower alkyl; $R_4$ is selected from the group consisting of hydrogen, lower alkyl, lower alkanoyloxy and hydroxy; $R_5$ and $R_6$ are each selected from the group consisting of hydrogen, trifluoromethyl and halogen and $R_{10}$ is selected from the group consisting of hydrogen and $C_1$-$C_6$, preferably $C_1$-$C_4$-lower alkyl.

As is indicated above, compounds wherein D is pyridyl are novel. Compounds wherein D includes a phenyl group are known.

By the term "lower alkyl" as utilized herein, either alone or in combination with another radical unless otherwise indicated, there is intended a straight or branched chain $C_1$-$C_7$, preferably $C_1$-$C_4$ hydrocarbon group, such as methyl, ethyl, propyl, isopropyl, butyl and the like.

The term "lower alkanoyloxy" represents a $C_1$-$C_7$, most preferably a $C_1$-$C_4$-lower alkyl carbonyloxy group containing the acyl moiety of a lower alkanoic acid. Such lower alkyl carbonyloxy group may be illustrated by acetoxy, propionyloxy, butryloxy and the like. The term "halogen" as found herein connotes all four forms thereof, i.e., fluorine, chlorine, bromine and iodine, unless otherwise indicated, in the compounds identified herein where appropriate.

In one embodiment, $R_2$ and $R_6$ are preferably both hydrogen. Preferably, $R_{10}$ is methyl. In a preferred embodiment, $R_2$ and $R_6$ are both hydrogen and $R_1$ is selected from the group consisting of nitro and halogen; most preferably, chlorine and bromine, and $R_{10}$ is methyl. Especially preferred are $R_2$ and $R_6$ as hydrogen, $R_{10}$ as methyl and $R_1$ as halogen and nitro, and when halogen, the group chlorine. $R_3$ is preferably hydrogen; $R_4$ is preferably hydroxy or hydrogen; most preferably, hydrogen. $R_5$ is preferably hydrogen and halogen, most preferably, chlorine and fluorine and when $R_5$ is halogen, in a preferred embodiment it is joined to the 2-position of the phenyl ring. When $R_5$ is halogen and in the 2-position, $R_6$ may also be halogen in one aspect and be present in the 6-position of the phenyl ring. Most preferred is a compound wherein $R_1$ is chlorine and nitro; $R_2$, $R_3$, $R_4$ and $R_6$ are hydrogen and $R_{10}$ is methyl. In addition, when D is phenyl, preferably $R_5$ is fluorine and is joined to the 2-position of the 5-phenyl ring. $R_2$ is preferably in the 8-position of the benzodiazepine nucleus of compounds I and Ia.

Compounds of the formula I and Ia above wherein D is pyridyl are novel compounds. Preferably, when D is pyridyl, it is a 2-pyridyl grouping.

The compounds of the formulae I and Ia above in the first process step are prepared by reacting a compound selected from the group consisting of a compound of the formulae

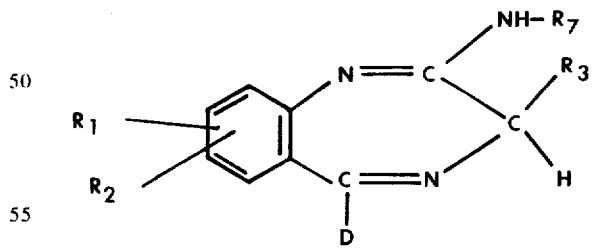

II and

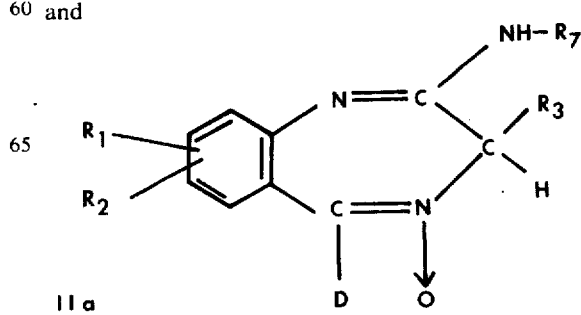

IIa wherein D, R₁, R₂ and R₃ are as above
and R₇ is lower alkyl (preferably methyl)
with nitrous acid whereby to obtain a compound of the formulae

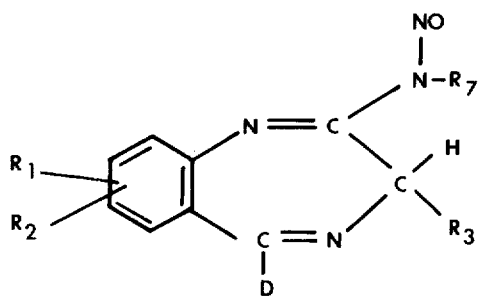

III and

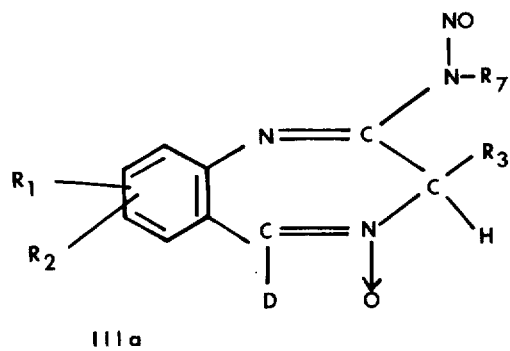

IIIa wherein D, R₁, R₂, R₃ and R₇ are as above.

The compounds of the formula III and IIIa above are novel and hence constitute a part of the present invention.

Conveniently, the nitrous acid is provided to the reaction zone by adding to the solution of a compound of the formula II or IIa above, an alkali metal nitrite, preferably, sodium nitrite. It is, of course, to be understood that the nitrous acid need not be provided to the reaction zone in the manner described above. The same end can be accomplished as follows:

A compound of the formula II or IIa above can be added to a solvent such as an alcohol, e.g., methanol, ethanol and the like or a lower alkanoic acid, such as acetic acid, propionic acid, and the like. To the so-formed solution, there is added a lower alkyl nitrite such as methyl, ethyl or amyl nitrite.

The treatment with nitrous acid in either embodiment is permitted to proceed at above or below room temperature, preferably at room temperature or below, to the desired compound of the formula III or IIIa above. Preferably, temperatures from about −5° to about 25°C. are preferred.

In the next step of the novel preparative approach described herein, a compound of the formula III or IIIa above is treated with hydrazine, preferably anhydrous hydrazine, whereby a compound of the formulae

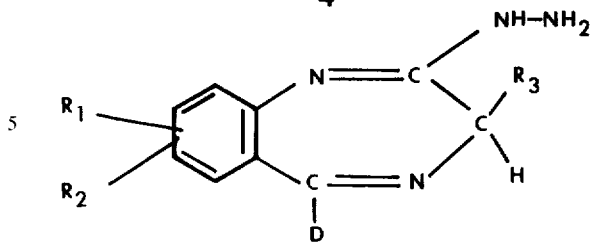

IV and

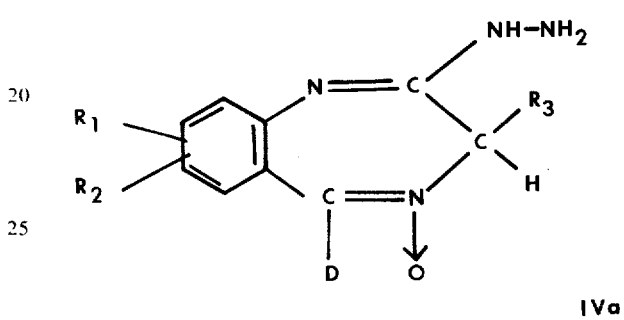

IVa wherein D, R₁, R₂ and R₃ are as above, is obtained.

Suitably, the second stage of the process aspect is effected in the presence of an organic solvent which may suitably be an ether such as diethyl ether, tetrahydrofuran and the like, a lower alkanol such as methanol, ethanol, propanol and the like or mixtures of the two. Suitably, the reaction is effected at about room temperature, although temperatures between the range of 20°C. to about 60°C. are most suitable for the purposes of the present invention.

The so-obtained compounds of the formula IV and IVa above are treated with a tri-lower alkyl-ortho-lower alkanoylate, preferably in the presence of an inert organic solvent whereby the corresponding compounds of the formula I or Ia are obtained. Representatives of tri-lower alkyl-ortho-lower alkanoylates are trimethyl-orthoacetate, triethyl-orthoacetate, triethyl-orthoformate, triethyl-orthopropionate, triethyl-orthobutyrate and the like. As should be evident, the "alkane" portion of the lower alkanoylates determines the R₁₀ grouping. Thus, for example, triethyl-orthoformate provides R₁₀ as H, trimethyl-orthoacetate provides R₁₀ as methyl, triethyl-orthopropionate provides R₁₀ as ethyl, and the like.

As inert solvents utilizable for the purposes of the present invention, there can be included lower alkanols, such as ethanol, methanol, propanol and the like; ethers such as tetrahydrofuran, diethyl ether and the like, dimethylsulfoxide, dimethylformamide and other suitable inert organic solvents.

All that is required of the solvent in the last-described steps as well as in the steps which precede the last-described step is that the starting benzodiazepine be sufficiently soluble in the solvent and that the inert solvent does not interfere with the ongoing reaction.

Suitably the last step is effected in the presence of an acid promotor. Any strong acid such as hydrohalic acid, e.g. hydrochloric acid, para-toluene sulfonic acid and the like would be suitable for use as the acid promotor. Temperature is not critical to a successful performance of the last process step; however, elevated temperatures are preferred, i.e. temperatures from about 30° to about the reflux temperature of the reaction mixture. In the most preferred aspect of the last step, the reaction is effected under reflux conditions.

In an alternate process aspect, compounds of the formula I and Ia above can be prepared directly from the corresponding compounds of the formula III and IIIa above by treating the latter with a lower alkanoyl hydrazide such as $C_1$-$C_7$, preferably a $C_1$-$C_4$ lower alkanoyl hydrazide such as acetyl hydrazide, propionyl hydrazide, butyryl hydrazide and the like in the presence of an inert organic solvent such as lower alkanol, e.g. ethanol, propanol, butanol and the like, dimethylformamide, ethers, such as diglyme and methoxy ethanol or any other suitable inert organic solvents. This process aspect is effected preferably at elevated temperatures, most preferably at about the reflux temperature of the reaction medium. The reaction proceeds in the presence of a strong base, such as amines, e.g. tertiary amines such as triethylamine, methyl piperidine and the like.

As above, the lower alkanoyl moiety determines the character of the $R_{10}$ grouping, e.g. acetyl provides $R_{10}$ as methyl.

When proceeding accordingly, there is also prepared a compound selected from the group consisting of a compound of the formula

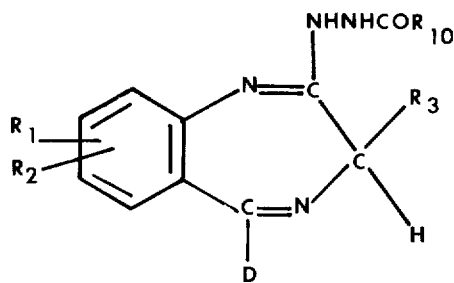

V wherein $R_1$, $R_2$, $R_3$, $R_{10}$ and D are as above.

The compounds of the formula I and V and compounds of the formula Ia and Va can be separated from the reaction medium in which they are prepared by usual procedures, e.g. crystallization and/or chromatography.

The compound of the formula V or Va above wherein $R_1$ and $R_2$ are other than nitro can be converted into the corresponding compound of the formula I, if desired, by the treatment thereof with a trilower alkyl phosphite such as trimethyl phosphite, triethyl phosphite or the like in the presence of any suitable inert organic solvent such as diglyme.

As is noted above in addition to the novel compounds of the formula I and Ia above wherein D is pyridyl, there is also encompassed within the purview of the present invention the acid addition salts thereof. The compounds of the formula I and Ia wherein D is pyridyl, preferably 2-pyridyl, form acid addition salts with pharmaceutically acceptable inorganic and organic acids, such as hydrohalic acid, e.g. hydrochloric acid, hydrobromic acid, sulfuric acid, phosphoric acid, nitric acid, citric acid, p-toluene sulfonic acid, ethyl sulfonic acid, ascorbic acid, salicylic acid and the like.

Compounds of the formula Ia above wherein $R_3$ is hydrogen (i.e. compounds which contain a N-oxide group) can be converted into the corresponding compounds of the formula I above wherein $R_4$ is lower alkanoyloxy by treating the compound of the formula Ia above with a reagent capable of providing a lower alkanoyl group. By rearranging a compound of the formula Ia which contains the N-oxide group with, i.e. agents capable of providing a lower alkanoyl group, a compound of the formula I above wherein $R_4$ is lower alkanoyloxy is obtained. The rearrangement can be effected with any suitable agent capable of effecting rearrangement and representative of such are lower alkanoic acids, lower alkanoyl anhydrides or lower alkanoyl halides. Representative of these are acetic acid, propionic acid, butyric acid, acetyl chloride, acetic anhydride, propionyl anhydride, butyryl anhydride, butyryl chloride and the like. The rearrangement is effected at elevated temperatures, e.g. temperatures up to about the reflux temperature of the reaction medium. Suitably, the reaction is effected in the presence of any inert organic solvent and among the many suitable for this purpose can be included toluene, chlorinated hydrocarbons such as methylene chloride, chlorobenzene and the like.

The so-obtained compound of the formula I wherein $R_4$ is lower alkanoyloxy can be hydrolyzed to the corresponding compound of the formula I wherein $R_4$ is hydroxy by hydrolysis. This hydrolysis can be effected in the presence of alkali which can be suitably provided to the reaction zone by the addition of sodium hydrox-

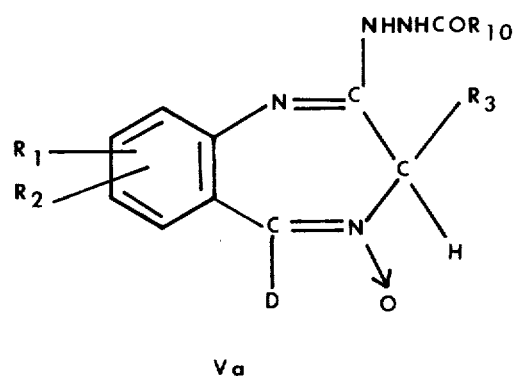

Va ide or any equivalent alkali metal hydroxide. This reaction suitably is effected in the presence of an inert organic solvent such as an ether, e.g. tetrahydrofuran ether, or an alkanol such as ethanol.

Compounds of the formula Ia above can be converted into the corresponding compound of the formula I above wherein $R_4$ is hydrogen or lower alkyl by treating the compound of the formula Ia above with any reagent capable of removing the oxygen of the nitrone grouping in accordance with conventional practice, e.g. by reduction with phosphorus trichloride or with hydrogen in the presence of a Raney nickel catalyst. Similarly, the N-oxide group can be removed from compounds of the formula IIa, IIIa, IVa and Va above.

Compounds of the formula I and Ia above and their pharmaceutically acceptable acid addition salts are useful as muscle relaxants, sedatives, and anticonvulsants. As contemplated by this invention, the novel compounds of the formula I and Ia above wherein D is pyridine and their acid addition salts can be embodied in pharmaceutical dosage formulations containing from about 1 to about 40 mg. of ingredient. Dosage can be conveniently adjusted to species and individual requirements. The novel compounds of the present invention and their pharmaceutically acceptable salts can be administered internally for example, parenterally or enterally in conventional pharmaceutical dosage forms. For example, there can be incorporated in conventional liquid or solid vehicals such as water, gelatin, starch, magnesium stearate, talc, vegetable oil and the like to provide tablets, elixirs, capsules, emulsions and the like according to acceptable pharmaceutical practices.

The following examples are illustrative but not limitative of the present invention. All temperatures are stated in degrees Centigrade.

Example 1

18 g. (0.26 mol) of sodium nitrite was added in small portions to a stirred solution of 60 g. (0.2 mol) of 7-chloro-2-methylamino-5-phenyl-3H-1,4-benzodiazepine 4-oxide in 400 ml. of glacial acetic acid over a period of 30 minutes. After addition, the mixture was stirred for another 30 minutes at room temperature.

The product was precipitated in crystalline form by gradually adding 400 ml. of water. The precipitate was collected, washed with water and dissolved in 500 ml. of methylene chloride. The solution was washed with saturated sodium bicarbonate solution, dried over sodium sulfate and concentrated. After addition of 200 ml. of isopropanol, the rest of the methylene chloride was evaporated under reduced pressure.

The crystals were collected, washed with 2-propanol and dried to leave 7-chloro-2-(N-nitrosomethylamino)-5-phenyl-3H-1,4-benzodiazepine 4-oxide as light yellow material with a melting point of 158°–160° dec. After recrystallization from ether/hexane, the product melted at 158°–160° dec.

EXAMPLE 2

10 ml. of anhydrous hydrazine was added to a solution of 10 g. of 7-chloro-2-(N-nitrosomethylamino)-5-phenyl-3H-1,4-benzodiazepine 4-oxide in 100 ml. of tetrahydrofuran and 50 ml. of methanol. After sitting at room temperature for 1 hour, the reaction mixture was evaporated under reduced pressure. The crystalline residue was partitioned between methylene chloride and water. The methylene chloride solution was dried and evaporated. Crystallization from methylene chloride/ether yielded 7-chloro-2-hydrazino-5-phenyl-3H-1,4-benzodiazepine 4-oxide with a melting point of 290°–292° dec.

EXMAPLE 3

1.5 ml. of acetic anhydride was added to a solution of 2.5 g. of 7-chloro-2-hydrazino-5-phenyl-3H-1,4-benzodiazepine 4-oxide in 50 ml. of methylene chloride. After stirring for 15 minutes at room temperature, the mixture was concentrated and crystallized by addition of ether to yield 2-(2-acetylhydrazino)-7-chloro-5-phenyl-3H-1,4-benzodiazepine 4-oxide, which after recrystallization from dimethylformamide, had a melting point of 272°–275° dec.

EXAMPLE 4

A mixture of 13.5 g. of 7-chloro-2-hydrazino-5-phenyl-3H-1,4-benzodiazepine 4-oxide, 200 ml. of ethanol, 9 ml. of triethylorthoacetate and 0.5 g. of p-toluenesulfonic acid was refluxed for 20 minutes. The ethanol was removed under reduced pressure. The residue was partitioned between methylene chloride and aqueous sodium carbonate solution. The methylene chloride layer was dried and evaporated. The remaining crystals were recrystallized from ethyl acetate to yield 8-chloro-1-methyl-6-phenyl-4H-s-triazolo[4,3-a][1,4]benzodiazepine 5-oxide with a melting point of 280°–282°.

EXAMPLE 5

A solution of 7.5 g. of 8-chloro-1-methyl-6-phenyl-4H-s-triazolo[4,3-a][1,4]benzodiazepine 5-oxide in 100 ml. of acetic anhydride was refluxed for 1 hour. The reagent was evaporated, at the end azeotropically with xylene, and the residue was crystallized from ethyl acetate to yield 4-acetoxy-8-chloro-1-methyl-5-phenyl-4H-s-triazolo[4,3-a][1,4]benzodiazepine with a melting point of 233°–235°.

EXAMPLE 6

40 ml. of 1N sodium hydroxide solution was added to a solution of 5 g. of 4-acetoxy-8-chloro-1-methyl-6-phenyl-4H-s-triazolo[4,3-a][1,4]benzodiazepine in 100 ml. of tetrahydrofuran and 100 ml. of ethanol.

After sitting for 15 minutes at room temperature, the reaction mixture was acidified by adding 5 ml. of glacial acetic acid and was concentrated under reduced pressure. The separated crystalline product was collected, washed with water and recrystallized from ethanol to give 8-chloro-4-hydroxy-1-methyl-6-phenyl-4H-s-triazolo[4,3-a][1,4]benzodiazepine, having a melting point of 247°–252°.

EXMAPLE 7

A solution of 63.2 g. (0.2 mol) of 7-bromo-1,3-dihydro-5-(2-pyridyl)-2H-1,4-benzodiazepin-2-one in 1.7 l. of tetrahydrofuran and 400 ml. of benzene was saturated with methylamine. A solution of 45.5 g. of titanium tetrachloride in 400 ml. of benzene was added slowly with ice cooling. After addition was complete, the reaction mixture was stirred and refluxed for 2 hours. It was then partitioned between water and methylene chloride. The organic layer was dried over sodium sulfate and evaporated. Crystallization from methylene chloride/hexane yielded 7-bromo-2-methylamino-5-(2-pyridyl)-3H-1,4-benzodiazepine, having a melting point of 208°–214°.

EXAMPLE 8

4.3 g. (0.0625 mol) of sodium nitrite was added in small portions to a stirred solution of 16.4 g. (0.05 mol) of 7-bromo-2-methylamino-5-(2-pyridyl)-3H-1,4-benzodiazepine in 200 ml. of glacial acetic acid. After addition (15 minutes), the mixture was stirred for 30 minutes at room temperature, diluted with water and extracted with ether. The extracts were washed with saturated sodium bicarbonate solution, dried over sodium sulfate and evaporated, giving crude 7-bromo-2-(N-nitrosomethylamino)-5-(2-pyridyl)-3H-1,4-benzodiazepine as an oil. 2 g. of the remaining oil was chromatographed over 60 g. of silica gel using 10 percent ethanol in methylene chloride. The clean fractions were combined and evaporated. The residue was stirred in isopropanol overnight, whereupon crystalline 7-bromo-2-(N-nitrosomethylamino)-5-(2-pyridyl)-3H-1,4-benzodiazepine separated, m.p. 102°–106°.

EXAMPLE 9

13 ml. of anhydrous hydrazine was added to a solution of 13 g. of the above crude 7-bromo-2-(N-nitrosomethylamino)-5-(2-pyridyl)-3H-1,4-benzodiazepine as an oil in 50 ml. of tetrahydrofuran and 50 ml. of methanol. The mixture was stirred for 1 hour at room temperature and seeded with product obtained from pure nitroso compound. The separated crystals were collected, washed with methanol to yield 7-bromo-2-hydrazino-5-(2-pyridyl)-3H-1,4-benzodiazepine, having a melting point of 230°–233°.

EXAMPLE 10

A mixture of 2.9 g. of 7-bromo-2-hydrazino-5-(2-pyridyl)-3H-1,4-benzodiazepine, 50 ml. of ethanol, 2 ml. of triethylorthoacetate and 0.2 g. of p-toluenesulfonic acid was refluxed for 20 minutes. The solvent was evaporated under reduced pressure and the residue was partitioned between methylene chloride and aqueous sodium carbonate solution. The organic phase was dried and evaporated. Crystallization from methylene chloride/hexane yielded 8-bromo-1-methyl-6-(2-pyridyl)-4H-s-triazolo[4,3-a][1,4]-benzodiazepine, having a melting point of 245°–248°. Chromatography of the mother liquor on 60 g. of silica gel using 10 percent ethanol in methylene chloride afforded additional product, m.p. 248°–250°.

EXAMPLE 11

A mixture of 3.3 g. of N-nitrosochlordiazepoxide, 30 ml. of ethanol, 3 ml. of triethylamine and 2 g. of acetyl hydrazide was refluxed for 24 hours. The solvent was removed and replaced by n-butanol. After additional 24 hours of reflux, the reaction mixture was evaporated. The residue was slurried with methylene chloride. The insoluble material was collected and recrystallized from methylene chloride/ethanol to yield 2-(2-acetylhydrazino)-7-chloro-5-phenyl-3H-1,4-benzodiazepine 4-oxide. The methylene chloride soluble part was chromatographed over 70 g. of silica gel using 10 percent ethanol in methylene chloride. Crystallization of the clean fractions from ethyl acetate yielded 8-chloro-1-methyl-6-phenyl-4H-s-triazolo[4,5-a][1,4]benzodiazepine 5-oxide with a melting point of 278°–282°.

EXAMPLE 12

A tablet formulation can be prepared as follows:

|  | Per Tablet |
|---|---|
| 8-bromo-1-methyl-6-(2-pyridyl)-4H-s-triazolo(4,3-a)(1,4)benzodiazepine | 5.00 mg. |
| Dicalcium phosphate dihydrate, unmilled | 195.00 mg. |
| Corn starch | 24.00 mg. |
| Magnesium stearate | 1.00 mg. |
| Total Weight | 225.00 mg. |

Procedure:

1. 8-Bromo-1-methyl-6-(2-pyridyl)-4H-s-triazolo(4,3-a)(1,4)-benzodiazepine and corn starch were mixed together and passed through a No. 00 screen in Model "J" Fitz with hammers forward.

2. This premix was then mixed with dicalcium phosphate and one-half of the magnesium stearate, passed through a No. 1A screen in Model J Fitz with knives forward and slugged.

3. The slugs were passed through a No. 2A plate in a Model "D" Fitz at slow speed with knives forward, and the remaining magnesium stearate was added.

4. The mixture was mixed and compressed.

EXAMPLE 13

A capsule formulation can be prepared as follows:

|  | Per capsule |
|---|---|
| 8-bromo-1-methyl-6-(2-pyridyl)-4H-s-triazolo(4,3-a)(1,4)benzodiazepine | 10 mg. |
| Lactose, USP | 165 mg. |
| Corn starch, USP | 30 mg. |
| Talc, USP | 5 mg. |
| Total Weight | 210 mg. |

Procedure:

1. 8-Bromo-1-methyl-6-(2-pyridyl)-4H-s-triazolo(4,3-a)(1,4)benzodiazepine, lactose and corn starch were mixed in a suitable mixer.

2. The mixture was further blended by passing through a Fitzpatrick Comminuting Machine with a No. 1A screen with knives forward.

3. The blended powder was returned to the mixer, the talc added and blended thoroughly.

4. The mixture was filled into No. 4 hard shell gelatin capsules on a Parke Davis capsulating machine. (Any similar type capsulating machine may be used.)

EXAMPLE 14

A suppository formulation can be prepared as follows:

|  | Per 1.3 gm. Suppository |
|---|---|
| 8-bromo-1-methyl-6-(2-pyridyl)-4H-s-triazolo(4,3-a)(1,4)benzodiazepine | 0.010 gm. |
| Wecobee M* | 1.245 gm. |
| Carnauba wax | 0.045 gm. |

*E.F. Drew Company
522 Fifth Avenue
New York, New York

Procedure:

1. The Wecobee M and the carnauba wax were melted in a suitable size glass lined container (stainless steel may also be used), mixed well and cooled to 45°C.

2. The 8-bromo-1-methyl-6-(2-pyridyl)-4H-s-triazolo(4,3-a)(1,4)benzodiazepine, which had been reduced to a fine powder with no lumps, was added and stirred until completely and uniformly dispersed.

3. The mixture was poured into suppository molds to yield suppositories having an individual weight of 1.3 gm.

4. The suppositories were cooled and removed from molds. They were then individually wrapped in wax paper for packaging (foil may also be used).

EXAMPLE 15

A parenteral formulation can be prepared as follows:

|  | Per cc |  |
|---|---|---|
| 8-bromo-1-methyl-6-(2-pyridyl)-4H-s-triazolo(4,3-a)(1,4)benzodiazepine | 0.5 | mg. |
| Propylene glycol | 0.4 | cc |
| Benzyl alcohol (benzaldehyde free) | 0.015 | cc |
| Ethanol 95% USP | 0.10 | cc |
| Sodium Benzoate | 48.8 | mg. |
| Benzoic Acid | 1.2 | mg. |
| Water for Injection q.s. | 1.0 | cc |

Procedure: (for 10,000 cc)

1. The 5 gm. of 8-bromo-1-methyl-6-(2-pyridyl)-4H-s-triazolo(4,3-a)(1,4)benzodiazepine were dissolved in 150 cc of benzyl alcohol; 4,000 cc of porpylene glycol and 1,000 cc of ethanol were added.

2. The 12 gm of benzoic acid were dissolved in the above. The 488 gm. of sodium benzoate dissolved in 3,000 cc of Water for Injection were added. The solution was brought up to final volume of 10,000 cc with Water for Injection.

3. The solution was filtered through an O2 Selas candle, filled into suitable size ampuls, gassed with N₂ and sealed. It was then autoclaved at 10 psi for 30 minutes.

In a similar manner as in Example 1, there can be prepared
1. 7-chloro-2-(N-nitrosomethylamino)-5-(2-fluorophenyl)-3H-1,4-benzodiazepine 4-oxide;
2. 7-nitro-2-(N-nitrosomethylamino)-5-phenyl-3H-1,4-benzodiazepine 4-oxide;
3. 7-chloro-2-(N-nitrosomethylamino)-5-(2,6-dichlorophenyl)-3H-1,4-benzodiazepine 4-oxide;
4. 7-chloro-2-(N-nitrosomethylamino)-5-(2,6-difluorophenyl)-3H-1,4-benzodiazepine 4-oxide; and
5. 7-bromo-2-(N-nitrosomethylamino)-5-(2-pyridyl)-3H-1,4-benzodiazepine 4-oxide.

In a manner similar to that described in Examples 7–10, there can be prepared
1. 8-chloro-1-methyl-6-(2-pyridyl)-4H-s-triazolo[4,3-a][1,4]benzodiazepine;
2. 8-bromo-1-ethyl-6-(2-pyridyl)-4H-s-triazolo[4,3-a][1,4]benzodiazepine; and
3. 8-nitro-1-methyl-6-(2-pyridyl)-4H-s-triazolo[4,3-a][1,4]benzodiazepine.

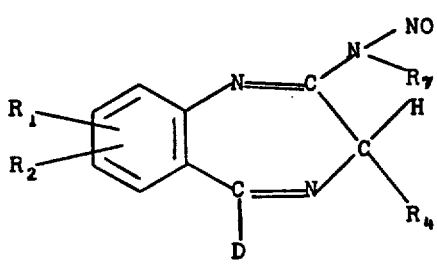

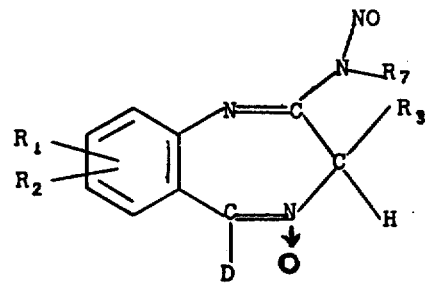

We claim:
1. A compound selected from the group consisting of wherein D is selected from the group consisting of

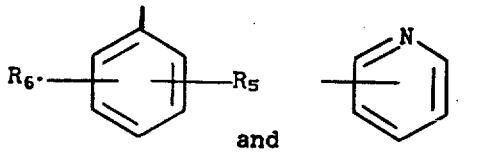

$R_1$ and $R_2$ are each selected from the group consisting of hydrogen, halogen, nitro and trifluoromethyl; $R_3$ is selected from the group consisting of hydrogen and lower alkyl; $R_4$ is selected from the group consisting of hydrogen and lower alkyl;

$R_5$ and $R_6$ are selected from the group consisting of hydrogen, trifluoromethyl and halogen;
and $R_7$ is lower alkyl.

2. A compound as in claim 1 wherein $R_2$, $R_3$, $R_4$ and $R_6$ are all hydrogen.

3. A compound as in claim 2 wherein $R_7$ is methyl.

4. A compound as in claim 3 wherein $R_1$ is halogen and $R_5$ is hydrogen and halogen.

5. A compound as in claim 4 of the formula 7-chloro-2-(N-nitrosomethylamino)-5-phenyl-3H-1,4-benzodiazepin-4-oxide.

6. A compound as in claim 1 of the formula 7-bromo-2-(N-nitrosomethylamino)-5-(2-pyridyl)-3H-1,4-benzodiazepine.